United States Patent [19]

Menton

[11] Patent Number: 5,032,124
[45] Date of Patent: Jul. 16, 1991

[54] INSTRUMENT FOR THE SURGICAL REMOVAL OF A PIECE OF TISSUE

[76] Inventor: Michael Menton, Ursrainer Ring 103, 7400 Tubingen, Fed. Rep. of Germany

[21] Appl. No.: 405,177

[22] Filed: Sep. 11, 1989

[30] Foreign Application Priority Data

Sep. 21, 1988 [DE] Fed. Rep. of Germany ....... 3831967

[51] Int. Cl.⁵ .............................................. A61N 5/06
[52] U.S. Cl. ...................................... 606/19; 606/14; 606/18; 128/395
[58] Field of Search ...................... 128/395, 397, 398; 606/2, 10, 13-19

[56] References Cited

U.S. PATENT DOCUMENTS

| | | | |
|---|---|---|---|
| 3,804,095 | 4/1974 | Bredemeier | 606/14 |
| 3,913,582 | 10/1975 | Sharon | 606/19 |
| 4,563,565 | 1/1986 | Kampfer et al. | 219/121.19 |
| 4,672,969 | 6/1987 | Dew | 606/16 |
| 4,726,368 | 2/1988 | Morris | 606/151 |
| 4,750,486 | 6/1988 | Butler et al. | 606/18 |

FOREIGN PATENT DOCUMENTS 2309205 10/1973 Fed. Rep. of Germany .
2949278 5/1982 Fed. Rep. of Germany .

OTHER PUBLICATIONS

American Heritage Dictionary (3 pages).

Primary Examiner—David Shay
Attorney, Agent, or Firm—Browdy and Neimark

[57] ABSTRACT

An instrument for the surgical removal of a conical piece of tissue having an aperture from a human or other animal body using a laser beam has a laser beam guide housing which is made up of a tube, through which the inlet laser beam passes, of an inlet deflecting member for deflecting the laser beam from its inlet direction and of an outlet deflecting member, arranged at a lateral distance from the latter, to deflect the beam along an outlet direction thereof so that on twisting the guide housing about the inlet direction the emerging laser beam sweeps out a conical surface. The outlet deflecting member is arranged on a boom member extending laterally from the tube. The instrument furthermore has a guide pin which centers the guide housing by being inserted in the tissue aperture. The guide pin and the guide housing are able to be rotated in relation to each other.

10 Claims, 3 Drawing Sheets

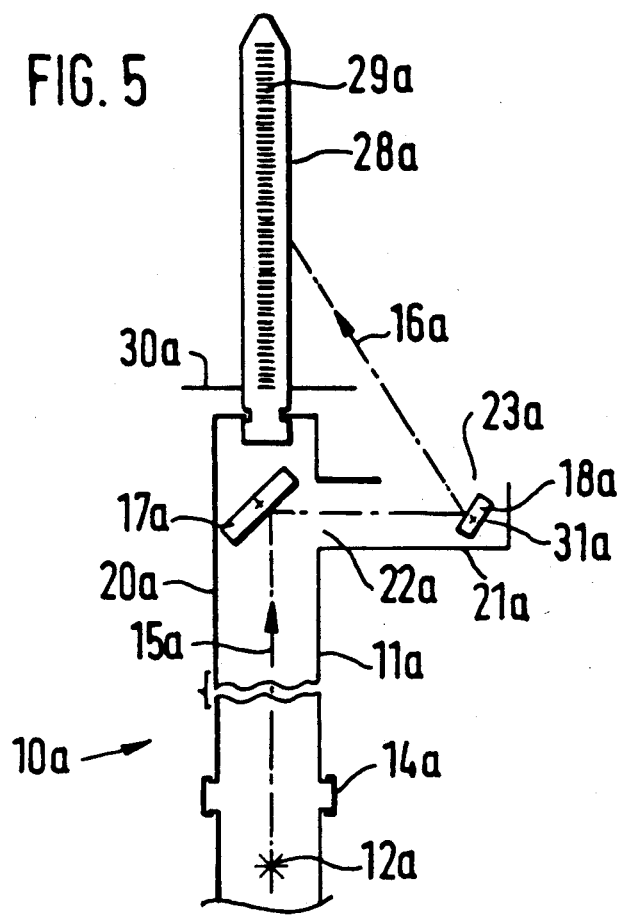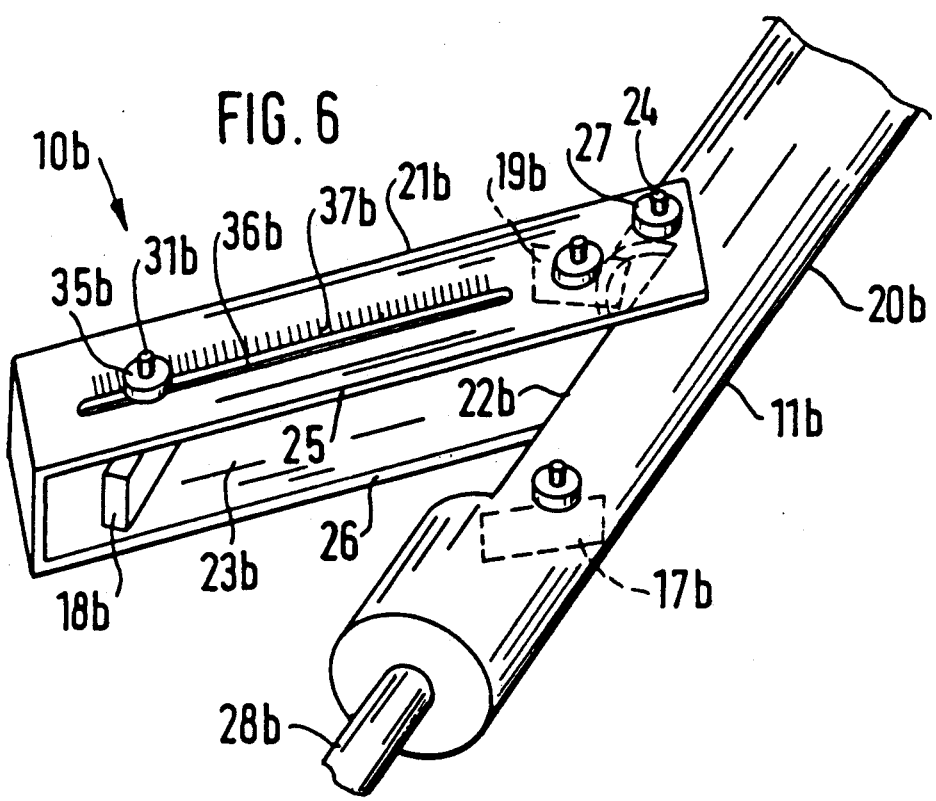

INSTRUMENT FOR THE SURGICAL REMOVAL OF A PIECE OF TISSUE

BACKGROUND OF THE INVENTION

The invention relates to an instrument for the surgical excision of a piece of tissue with a conical form and having an aperture, from a human or other animal body using a laser beam. Such an instrument may comprise a guide housing with a tube through which the incoming laser beam shines, an inlet deflecting member deflecting the laser beam out from its inlet direction, and an outlet deflecting member, offset laterally from the inlet deflecting member, for deflecting the laser beam along an outlet direction thereof so that on rotating the guide housing about the inlet path the emerging laser beam sweeps out a conical surface. The instrument is furthermore provided with a guide pin able to be plugged into the aperture for locating the guide housing during rotation.

The main parts of the human uterus are its body (corpus uteri) and its neck (cervix uteri). The neck of the uterus protrudes a few centimeters into the vagina. This lowermost section of the neck of the uterus is referred to as the external os uteri (portio). At the mouth of the womb there is histological transition between the uterine mucous membrane, which lines the entire uterine cavity, and integument tissue (squamous epithelium), which covers the part of the uterus protruding into the vagina. The transitional zone is termed the transformation zone, which is a regenerative section, in which cell differentiation takes place. Atypical cells are also derived from this regenerative section and after a certain latent period may start malignant growth. The areas, in which such cellular alterations take place, may usually be localized by special examination methods (colposcopy) of the cervix. If a timely diagnosis is made such preinvasive stages of carcinoma of the cervix uteri may be extirpated by the removal of a smaller or larger cone of tissue with a size dependent on the diagnosis made. Such an operation thus makes it possible to save the uterus, something that is extremely important for young patients in order to preserve fertility.

In order to perform this operation the German specification 2,309,205 has described an instrument of the initially mentioned type, which in use is introduced into the vagina so that its locating pin may be introduced into the os uteri. After switching on the laser the tube is rotated about the tube axis together with the inlet and outlet deflecting members so that the desired cone of tissue is cut out. As compared with conventional cutting using a knife, the method is substantially quicker and only lasts a few minutes. Furthermore the loss of blood is very small and there is hardly any postoperative hemorrhage. For this reason no secondary effects such as reduced fertility are likely. Furthermore the operation may be performed without hospitalization and the complication rate is negligible, while on the other hand conventional surgical methods involve a period in a hospital lasting about 8 days. A further advantage of such laser conization is that the extirpated cone may be readily examined pathologically after the operation.

However along with these advantages conization by a laser using the known instrument involves the following disadvantages:

The tube containing the deflecting parts in the form of mirrors is for its part borne in a stationary external tube. This design has to be radially symmetrical and thus takes up much space around it in the zone where the operation is being performed so that the site of the operation may only be observed using a microscope through the tube. In this respect only the actual point of cutting of the laser beam may be observed since the microscope light is deflected via the same mirrors to the site of the operation. Furthermore, owing to the lack of space available, the access of instruments to the site of the operation is limited.

A further shortcoming is to be seen in the fixed arrangement of the locating pin on the guide housing so that there is friction between the locating pin, which is entrained in rotation during the cutting out of the cone of tissue, and the tissue surrounding it so that the cone of tissue is subjected to torsion. This may mean that the conical form is imperfect and the cone of tissue may be torn out shortly before the end of the cutting operation. Furthermore the forces produced the centering of the locating pin may also be imperfect and this has an undesired effect on the resulting conical form.

This disadvantage is more likely prone to occur when the instrument is only held in the hand and is not held using a stationarily arranged external tube (so that in this case the external tube would perform the locating function).

SHORT SUMMARY OF THE INVENTION

Accordingly one object of the present invention is to devise an instrument of the initially described type which while still possessing the advantages described makes possible improved observation of the site of the operation.

A still further aim of the invention is to offer less obstruction to the introduction of other instruments.

Another object is to improve the centering or locating action achieved with the locating pin and to avoid the occurrence of friction on the cone which is to be excised.

In order to achieve these or other objects appearing from the instant specification claims and drawings, the guide housing has a lateral boom member extending from the tube on which the outlet deflecting member is arranged in the centering pin and the guide pin and the guide housing are able to be rotated in relation to each other.

Owing to the provision of the boom member there is a reduced cross section area of the guide housing so that the site of the operation is able to be seen by eye and is additionally accessible for instruments past the housing. Furthermore, when the guide housing is rotated the guide pin does not move so that the disadvantages otherwise occurring if the guide pin is entrained in rotation are avoided. Therefore more accurate centering is ensured and the cone of tissue is not subject to frictional forces and the form thereof is more perfect.

Although the German patent 2,949,278 has proposed a conizer which has a similar geometry as regards the possibility of observing the site of the operation, this instrument operates with a strip-like flexible knife and not with a laser, the knife having its end to be introduced into the os uteri mounted on the front end of a rod and having its opposite end held in a guide extending radially from the rod. This instrument is thus based on a completely different principle to the present invention.

Although primarily the instrument of the invention is intended for conization of the part of the cervix uteri adjacent to the vagina, it may in principle be used for excision in other parts of a human or other animal body.

Convenient further developments of the invention are described in the claims.

There will now follow a detailed description of the invention with reference to the accompanying drawings which show various possible embodiments thereof.

LIST OF THE SEVERAL VIEWS OF THE DRAWINGS

FIG. 5 shows a further embodiment of the invention diagrammatically in a manner similar to the showing of FIG. 1.

FIG. 6 is an oblique view, similar to that of FIG. 2, of part of a third embodiment of the invention.

DETAILED DESCRIPTION OF EMBODIMENTS OF THE INVENTION

Figure 1:
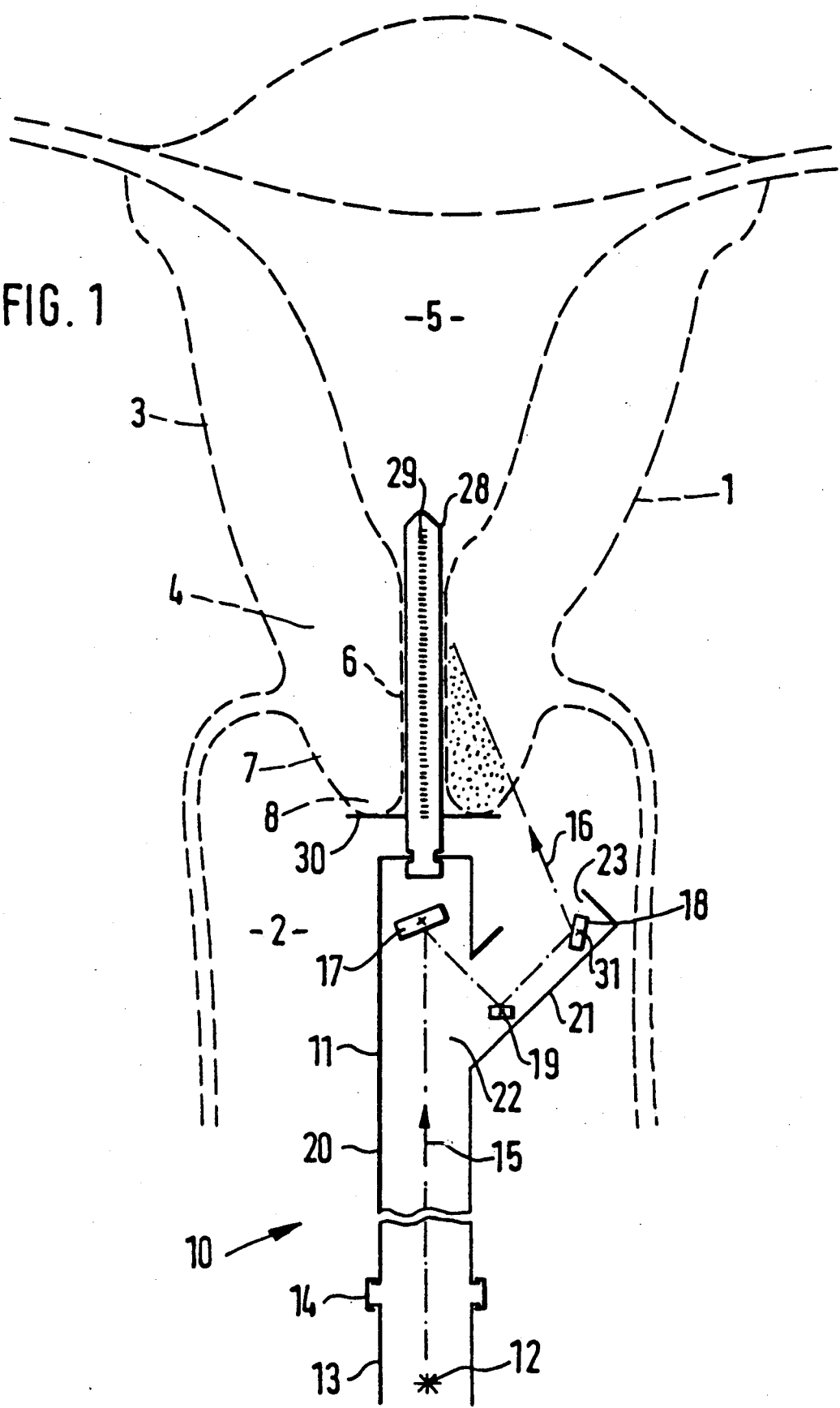
FIG. 1 shows an instrument in accordance with the invention in a diagrammatic view during use for excising a cone of tissue from the cervix uteri where the latter is adjacent to the vagina.

In FIG. 1 the human uterus 1 and the vagina 2 adjacent to it are marked in broken lines. The uterus or womb 1 consists of the corpus uteri 3 and the cervix uteri adjacent to the vagina 2. The os uteri 6 extends through the cervix 4 from the cavity 5 of the uterus into the vagina 2. The cervix uteri 4 protrudes a few centimeters into the vagina 2. This lowermost portion of the cervix uteri 4 constitutes the external os 7. There is a transition or transformation zone 8 adjacent to the os 7 and on it the mucous membrane lining the cavity 5 of the uterus merges into an integument tissue covering the part of the uterus protruding into the vagina 2. This zone constitutes a regenerative zone in which cellular differentiation takes place and in which it is also possible for atypical cells to be produced, which after a certain latent period may transform into malignant tissue. If a timely diagnosis is made these preinvasive stages of cervical carcinoma may be dealt with by excising a cone of tissue whose size depends on the actual diagnosis made, whose base is adjacent to the vagina 2 and whose apex is adjacent to the cavity 5 of the uterus.

Figure 2:
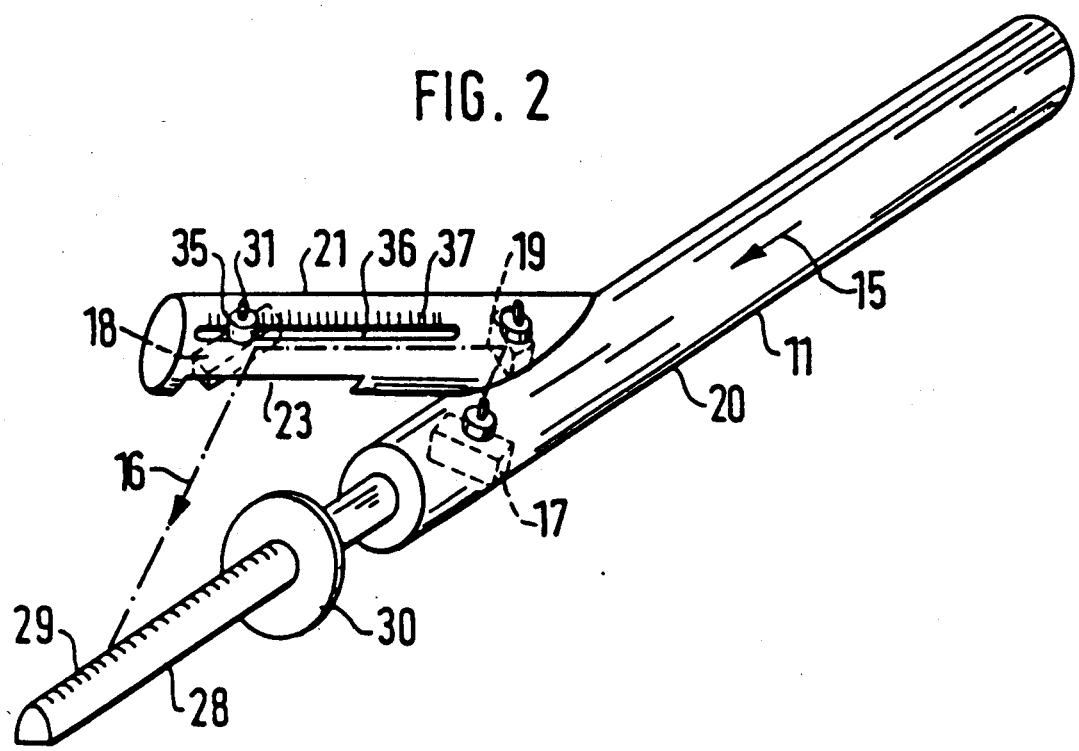
FIG. 2 is an oblique view of the instrument as shown in FIG. 1.
Figure 3:
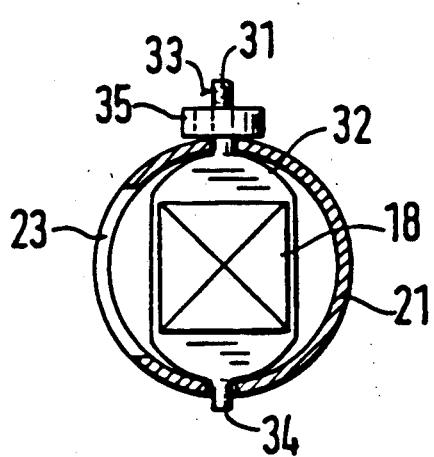
FIG. 3 shows the instrument of FIGS. 1 and 2 in a cross section taken through the boom member in the portion thereof comprising the outlet deflecting member.
Figure 4:
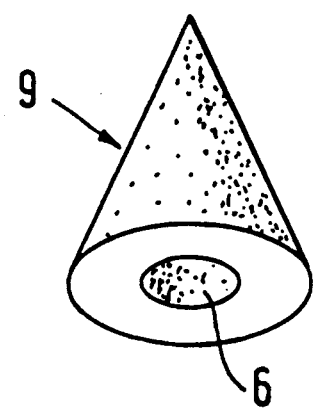
FIG. 4 is an oblique view of the excised cone of tissue.

In order to excise the tissue cone 9 separately indicated in FIG. 4 use is made of an instrument 10, which has a laser beam guide housing 11, which is connected with a laser beam generator 13 comprising a laser source 12. In this respect the laser beam guide housing 11 is connected in a rotary manner with the laser source 12 and, respectively, the laser beam generator 13, such connection being by way of an intermediate fitting 14 shown diagrammatically. The laser beam coming from the laser source 12 and marked in broken lines passes along the inlet direction 15 into to the guide housing 11 and leaves the latter in the outlet direction 16. The outlet direction 16 is at an acute angle to the inlet direction 15. The deflection of the laser beam is performed by means of a deflection device which is arranged in the guide housing 11 and which comprises an inlet deflecting member 17 deflecting the laser beam out of the inlet direction 15 or path and an outlet deflecting member 18 deflecting the laser beam along the outlet direction 16. In the present working embodiment of FIGS. 1 and 2 there is an intermediate deflecting member 19 located between the inlet deflecting member 17 and the outlet deflecting member 18 so that the laser beam is deflected by the inlet deflecting member 17 to the intermediate deflecting member 19 and then by the latter to the outlet deflecting member 18 and there is a zigzag path of the beam.

In any case the outlet deflecting member 18 is located so that it is laterally spaced from the inlet deflecting part 17, in which respect, as seen in the inlet direction 15 of the laser beam, the same may be arranged in front or behind in accordance with the local conditions. The outlet direction 16 is at such an acute angle to the inlet direction 15 that the emerging laser beam intersects an imaginary line extended past the inlet deflecting member 17.

The deflecting members 17, 18 and 19 of the deflecting device may be of conventional design, more particularly in the form of mirrors or prisms set at a suitable oblique angle.

The guide housing 11 with the deflecting device 17, 18 and 19 is able to be revolved about an axis of rotation which is aligned with the inlet direction 15 so that it is not separately indicated in the figure. If the guide housing 11 is revolved about this axis of rotation or, respectively, the inlet direction 15, then the deflecting device will be rotated as well and with it the laser beam emerging along the outlet direction 16. When this rotary motion takes place the laser beam will move as the generatrix of a conical surface whose cone axis is formed by the axis of rotation and whose cone base is adjacent to the deflecting device.

For use of the device 10 its guide housing 11 is moved into a position close to the piece of tissue to be excised so that the laser beam may impinge on the respective part of the body without obstruction. On rotating the guide housing 11 the laser beam will then excise the tissue cone 9. In the case of the working example of the invention shown in FIG. 1 the guide housing 11 is revolved in coaxial relation to the os uteri 6. Half of the longitudinal section area of the result tissue cone 9 is marked in dots in FIG. 1.

In the working example of the invention in question the guide housing 11 has an inlet guide tube 20 and a boom member 21 projecting laterally therefrom and carrying the deflecting member 18. At one end as mentioned the guide tube 20 is connected with the laser source 12 so that it and with it the boom member 21 may be turned in relation to the stationary laser source during the operation. At the opposite end of the guide tube 20, along which the entering laser beam passes, the inlet deflecting member 17 is arranged. In order for the laser beam deflected by the inlet deflecting member 17 to leave the guide tube 20, the latter has a suitably arranged lateral window 22. In the working example of FIGS. 1 and 2 the laser beam is deflected backwards somewhat by the inlet deflecting member 17 to the intermediate deflecting member 19, which is located adjacent to the transition between the guide tube 20 and the boom member 21. Then the laser beam passes through the boom member 21 obliquely forwards and outwards as far as the outlet deflecting member 18. Owing to this ray geometry the beam member 21 is arranged to extend at an acute angle from the guide tube 20. Furthermore the boom member 21 may be formed by a piece of tube which has an outlet aperture 23 for the laser beam.

The guide housing 11 consists of a metal and it is possible for the boom member 21 to be welded to the side of the guide tube 20.

In the case of the next working example as shown in FIG. 5 which in many respects is the same as FIG. 1 the intermediate deflecting member 19 is omitted. In this case the inlet deflecting member 17a deflects the laser beam directly to the outlet deflecting member 18a. In this case between the two deflecting members 17a and 18a the laser beam is directed so as to be generally normal to the inlet direction 15a. Accordingly the boom member 21a extends from the guide tube 20a so as to be generally normal thereto. Owing to the identity in other respects the working embodiment of FIG. 5 is not further described herein. The corresponding parts are denoted by like reference numerals with the addition of a small letter a.

While in the working examples in accordance with FIGS. 1 through 3 and 5 the boom member 21 and, respectively, 21a extends rigidly from the guide tube 20, in the design of FIG. 6 it is also possible for the boom member 21b carrying the outlet deflecting member 18b to rotatably connected with the guide tube 20b that the angle between the guide tube and the deflecting member may be adjusted. For this purpose the boom member 21b, formed for instance by a piece of U section open on the outlet side, is bearing on the guide tube 20b by means of a pivot pin 24. It will be clear that the boom member 21b is made with such dimensions that the pivoting action is not obstructed. Accordingly in the illustrated working example of the invention the distance between the two limbs 25 and 26 of the boom member 21b is greater than the diameter of the guide tube 20b so that the boom member on the pivoted end may extend over the guide tube. In order to lock the boom member 21b in the respective position into which it has been pivoted it is possible for the pivot pin 24 to be formed by a threaded pin for instance, which extends through the boom member 21b and the guide tube 20b and at one end carries a clamping member rigidly connected with it and at the other end carries a nut 27 which may be tightened to clamp the arrangement. With the exception of the pivoting arrangement of the boom member 21b this design as shown in FIG. 6 is the same as the design of FIGS. 1 through 3 so that further description thereof is not required.

Whether an instrument with or without an intermediate deflecting member 19 is to be preferred depends on the local geometry of the site of the operation. If there is only a limited amount of space around the uterus the arrangement of FIGS. 1 and 2 which projects less to the side will be more suitable.

In the design of FIG. 6 there is admittedly the best possible adaptation to the respective spatial circumstances but for different pivotal positions of the boom member 21b it may be necessary to readjust all the deflecting members 17b, 18b and 19b. On the other hand in the case of a rigidly arranged boom member, the inlet deflecting member 17 and, respectively, 17a and any intermediate deflecting member 19 present may always be kept in the same position independently of the size of the cone 9 of tissue to be excised. The dimensions of the cone of tissue may be varied by adjusting the outlet deflecting member 18 and, respectively, 18a alone, as will be described below.

In every working example of the invention at its end adjacent to the site of the operation when the instrument 10; 10a; and 10b has when in use a guide pin 28; 28a; and 28b or the like centered on a line parallel to the inlet direction 15 and 15a. This pin projects in the axial direction and is able to be inserted into an aperture in the piece of tissue to be excised, and is more especially to be inserted into the os uteri 6 so that the guide pin 28; 28a; and 28b or the like locates and centers the guide housing 11; 11a and 11b when the latter is turned. The guide pin 28; 28a and 28b thus extends in the axial direction in front of the end, which has the inlet deflecting part 17; 17a and 17b, of the guide tube 20; 20a and 20b and during the operation may be plugged into the respective aperture 6 in the body. The body aperture 6 thus functions as a bearing for the guide pin 28; 28a; and 28b and as a support for the entire guide housing 11; 11a and 11b so that the latter does not have to be located and centered at any other position and only has to be turned.

The guide pin 28; 28a and 28b or the like preferably extends as far as a point past the maximum cone height (to be described below) in the axial direction. This not only provides for a suitable centering action in the body aperture 6 but also involves further advantages. If in fact the guide pin 28; 28a and 28b or the like consists of a material not transparent to the laser beam and not reflecting it, the laser beam will end at the guide pin 28; 28a and 28b or the like whatever the dimensions of the tissue cone 9 so that the laser beam is not able to penetrate inwards into the tissue any further and is not able to cause undesired injuries. Furthermore the guide pin may serve for facilitating pre-operative adjustment of the direction 16 and 16a of the emerging laser beam. Prior to the operation the dimensions of the cone to be excised are in fact ascertained on the basis of a microscopic examination of the outer part of os uteri. The before the operation and before the instrument has been introduced into the body of the patient, the deflection device is so adjusted that the setting and direction of the emerging laser beam correspond to the desired cone. For this the surgeon may use a pilot laser (as for instance a helium-neon laser). This pilot laser beam impinges on the guide pin 28; 28a and 28b so that the point of impingement is visible. The axial setting of the point of impingement corresponds to the height of the cone and the connecting line between the point of impingement and the outlet deflecting member 18 corresponds to the cone angle so that the size of the cone base surface may also be seen.

The pre-operative adjustment of the deflecting device to be in accord with the desired dimensions of the cone may be facilitated if the there is a scale 29 and 29a on the guide pin 28; 28a and 28b or the like running in the axial direction. It is then possible to take a reading for the cone height which will have been computed in advance.

When performing the operation (after switching off the pilot laser) the guide pin 28; 28a and 28b is introduced into the uterus so far that the zero point of the scale 29 is at the same level as the base of the cone to be excised. In this respect handling the instrument may be further simplified by providing an abutment part 30 and 30a limiting the depth of insertion of the guide pin 28; 28a and 28b or the like into the body aperture 6, such part 30 and 30a preferably being in the form of an abutment ring arranged on the guide pin of the like and against which the zero point of the scale 29 and 29a is placed. Like the guide pin or the like and the guide housing the abutment ring should consist of a suitably selected metal.

After this the working laser source 12 is turned on and the guide housing 11; 11a and 11b is turned one of more times through 360°. In this respect the design is such that only the guide housing with the deflecting device is turned while the guide pin or the like remains stationary. For this purpose the guide housing is connected with the guide pin or the like in such a manner that relative rotation is possible. The rotary movement has to take place at such a rate that the laser beam is able to penetrate as far as the guide pin 28; 28a and 28b or the like. The rotation may have to be repeated until the cone of tissue may be removed from the rest of the os uteri. Persistent minor hemorrhage at the stump of the os uteri may be dealt with by laser treatment or coagulation.

For adjusting the desired setting and orientation of the emerging laser beam there are the following provisions For adjusting the cone angle the outlet deflecting part 18; 18a and 18b is arranged so that it may be pivoted and locked in the respective position of pivot. The respective axis of pivot is normal to the plane of the ray path and may for instance be formed by the outlet deflecting part or, respectively, a frame 32 or the like holding it, having two trunnions 33 and 34 (see FIG. 3, which also applies for the other working examples) mounted on the guide housing or, respectively, on the boom member 21; 21a and 21b. One of the trunnions, as for instance the trunnion 33, has a male thread thereon so that it is possible for a lock nut 35 and 35b to be screwed onto the part of the trunnion 33 projecting from the guide housing. If the lock nut 35 is slackened off, it is possible for the respective deflecting part to be pivoted from the outside, for example by gripping the trunnion 33. If the lock nut 35 is tightened, the deflecting member 18; 18a and 18b or its frame 32 or the like will be pressed from the inside against the wall surface of the guide housing until a firm clamping action is produced.

The radius of the cone base surface may be adjusted by arranging the outlet deflecting part 18; 18a; and 18b at a different distance, at which it may be locked, from the axis of rotation, aligned with the inlet direction 15; and 15a of the laser beam. In this respect this longitudinal adjustment of the outlet deflecting part may be more appropriately referred to as adjustment in the direction of the laser beam, along which the beam extends towards the outlet deflecting member. In the working embodiments shown in FIGS. 1 through 3 and 6 the adjustment thus takes place along the line connecting the outlet deflecting member 18; and 18b and the intermediate deflecting member 18; and 10b, whereas in the case of the working embodiment of FIG. 5 the adjustment is performed along the line connected the inlet deflecting member 17a and the outlet deflecting member 18a. Whatever the position of the outlet deflecting member the other deflecting members may then keep in their positions and their angular settings.

Thus simply by turning and by a longitudinal shift of the outlet deflecting member it is possible to set the desired cone configuration, the same being able to be freely selected.

In order to shift the outlet deflecting member on the guide housing or, respectively, on its boom member the latter has a suitable guide device, as for instance one such that the bearing pin 31; 31a and 31b or, respectively, the bearing trunnions 33 and 34, run in a slot 36 and 36b extending in the direction of shift. For shifting the outlet deflecting member the lock nut 35 and 35b is again slackened off and when the desired slot position has been reached it is then tightened up again.

As will also be seen from the drawing in this connection, the guide housing may have an externally readable scale 37 and 37b adjacent to the outlet deflecting member so that the distance from the axis of rotation or from the deflecting member arranged in front of it along the ray path, may be read off.

The inlet deflecting member 17; 17a and 17b and any intermediate member 19 and 19b present are also able to be turned about an axis perpendicular to the plane of the ray path. This turning may be caused in the same manner as in the case of the rotation of the outlet deflecting member. In this respect the angular setting of these deflecting members only has to be set once and may then be left unchanged so that this adjustment may be in fact undertaken by the manufacturer of the instrument.

It is also to be noted that the instrument should be made as small as possible in size in order to meet requirements in the field of application. The guide tube 10; 20a and 20b which is the main part of the guide housing, may also have a very small diameter of approximately 0.5 to 1 cm.

In the case of a modified form of the instrument, not illustrated here, the length of the guide tube may be adjusted since it is made of a number of telescoping sections.

There are also the following possibilities of further modification:

The scale 37 and 37b provided for measuring shift of the outlet deflecting member may be replaced by an electronic indicating system which would be operated by a computer. This computer would then be able to generate values for the diameter of the cone base surface and the cone height in relation to the zero mark on the guide pin 28; 28b and 28b taking into account the angular setting, that is to say the angular setting of the outlet deflecting member.

Furthermore it would be possible for a measuring unit to be incorporated in the guide pin or the like in order to indicate the impingement of the laser beam on the guide pin and to present the surgeon with an indication of the required speed of the rotary motion. Furthermore the rotary motion of the device might be caused by a drive motor rather than by hand, such motor being operated by such a measuring unit on the guide pin.

I claim:

1. An instrument for the surgical removal of a piece of tissue with a configuration similar to that of a cone and having an aperture therein by using a laser beam comprising:
    a laser to generate an inlet laser beam,
    a laser beam guide housing having
        a tube through which said inlet laser beam is able to pass,
        an inlet deflecting member adapted to deflect said beam out of an inlet direction thereof and an outlet deflecting member arranged at a lateral distance from the inlet deflecting member and arranged to deflect the laser beam along an outlet direction thereof out of said inlet direction, so that on twisting of the guide housing around the inlet direction of the beam the outlet laser beam sweeps along a conical surface.

a guide pin adapted to be introduced into the aperture of the tissue and serving to locate the guide housing during such twisting, said guide pin and said guide housing being able to be turned in relation to each other, and a boom member being part of the guide housing and extending laterally from the tube, said outlet deflecting member being arranged on the boom member.

2. The instrument as claimed in claim 1 wherein the guide pin consists of a material free of a reflecting action in respect of the laser beam.

3. The instrument as claimed in claim 1 wherein the guide pin is provided with a measuring scale extending in the axial direction.

4. The instrument as claimed in claim 1 comprising an abutment member arranged on the guide pin in order to limit the depth of penetration thereof into the aperture.

5. The instrument as claimed in claim 1 comprising an intermediate deflecting member placed between the inlet deflecting member and the outlet deflecting member in order to cause the beam to follow a zigzag path.

6. The instrument as claimed in claim 1 wherein the boom member extends from the tube at an acute angle.

7. The instrument as claimed in claim 1 wherein the boom member is pivotally connected with the tube.

8. The instrument as claimed in claim 1 wherein the outlet deflecting member is arranged on the guide housing so that it may be pivoted and locked in a respective position of pivoting in order to vary the angle of the cone and/or for varying the ratio of the cone base and is arranged on the housing at an adjustable distance, at which it may be locked, from the inlet beam direction.

9. The instrument as claimed in claim 8, wherein the guide housing is provided with a scale, able to be read by an observer to indicate the distance from said inlet laser beam direction to the axis of pivoting of the outlet deflecting member.

10. An instrument for the surgical removal of a piece of tissue with a configuration similar to that of a cone and having an aperture therein by using a laser beam comprising:

a laser to generate an inlet laser beam;

a rotatable laser beam guide housing comprising: a tube through which said inlet laser beam is able to pass;

an inlet deflecting member in said tube adapted to deflect said beam out of an inlet direction thereof;

a boom member extending laterally from said tube;

an outlet deflecting member positioned outside said tube on the boom member, said outlet deflecting member further deflecting the laser beam along an outlet laser beam direction thereof out of said inlet direction, a guide pin adapted to be introduced into the aperture of the tissue and cooperating to locate the guide housing during rotation;

said guide housing being able to rotate in relation to said guide pin;

wherein, rotation of the guide housing around the inlet laser beam direction sweeps the outlet laser beam along a conical surface.

* * * * *